United States Patent
Overes et al.

(10) Patent No.: US 8,252,059 B2
(45) Date of Patent: Aug. 28, 2012

(54) FULL-METAL DAMPENING INTERVERTEBRAL IMPLANT

(75) Inventors: Thomas Overes, Langendorf (CH); Cyril Voisard, Niederbipp (CH); Robert Frigg, Bettlach (CH); Silas Zurschmiede, Grenchen (CH); Beat Lechmann, Grenchen (CH)

(73) Assignee: Synthes USA, LLC, West Chester, PA (US)

( * ) Notice: Subject to any disclaimer, the term of this patent is extended or adjusted under 35 U.S.C. 154(b) by 336 days.

(21) Appl. No.: 12/640,618

(22) Filed: Dec. 17, 2009

(65) Prior Publication Data
US 2010/0152856 A1    Jun. 17, 2010

Related U.S. Application Data

(60) Provisional application No. 61/138,341, filed on Dec. 17, 2008.

(51) Int. Cl.
*A61F 2/44* (2006.01)
(52) U.S. Cl. .................................................. 623/17.15
(58) Field of Classification Search ...... 623/17.11–17.16
See application file for complete search history.

(56) References Cited

U.S. PATENT DOCUMENTS

| | | | |
|---|---|---|---|
| 6,395,035 B2 * | 5/2002 | Bresina et al. ............. | 623/17.15 |
| 7,419,506 B2 | 9/2008 | Hestad et al. | |
| 2002/0128714 A1 | 9/2002 | Manasas et al. | |
| 2007/0067037 A1 | 3/2007 | Studer | |
| 2007/0118225 A1 | 5/2007 | Hestad et al. | |
| 2007/0123990 A1 | 5/2007 | Sharifi-Mehr | |
| 2008/0161924 A1 | 7/2008 | Viker | |

FOREIGN PATENT DOCUMENTS

| WO | WO 00/23014 | 4/2000 |
|---|---|---|
| WO | WO 2007/075411 | 7/2007 |
| WO | WO 2008/022206 | 2/2008 |

* cited by examiner

*Primary Examiner* — Kevin T Truong
*Assistant Examiner* — Sameh Boles
(74) *Attorney, Agent, or Firm* — McKeon, Meunier, Carlin & Curfman, LLC (57) ABSTRACT

A flexible element that may be configured, among various uses, as an intervertebral implant for insertion into an intervertebral disc space between adjacent vertebral bodies or between two bone portions. The flexible element includes one or more struts extending from superior and inferior endplates and bending towards one another for connection with one or more internal beams.

15 Claims, 9 Drawing Sheets

FULL-METAL DAMPENING INTERVERTEBRAL IMPLANT

CROSS-REFERENCE TO RELATED APPLICATIONS

This application claims priority to U.S. Provisional Patent Application No. 61/138,341, filed Dec. 17, 2008, entitled "FULL-METAL DAMPENING INTERVERTEBRAL IMPLANT," the contents of which are hereby incorporated by reference in its entirety.

BACKGROUND OF THE INVENTION

The flexible motion segments of the human spine include at least a pair of adjacent vertebral bodies, an intervertebral disc adhered therebetween to provide a cushion and bind the vertebral bodies together, and a pair of facet joints, which are small stabilizing joints located between and behind the adjacent vertebral bodies. The facet joints and the intervertebral disc, with the help of various ligamentation, function in harmony as a three joint entity to prevent excessive motion, over-twisting, or toppling over of the spine and to preserve the flexibility needed to turn, look around, and move about.

Millions of people suffer from back pain. In some instances, in order to relieve back pain and/or to stabilize the spine, it becomes necessary to insert an intervertebral implant into the intervertebral disc space between adjacent vertebral bodies at one or more levels. Current implants however do not take into account all of the biomechanical aspects of the human spine, especially the interplay between the intervertebral disc and the facet joints. Generally speaking, intervertebral implants modify the patient's normal physiological spinal motions with consequences. For example on the actual range-of-motion of the segment or on shear loads acting on the different spine components (e.g., facet joint, facet capsule, ligaments, bone-implant interface, etc.). Thus current intervertebral implants do not result in a completely satisfactory solution. That is, current implants, whether unconstrained, semi-constrained or constrained, do not mimic an important feature of the intervertebral disc, namely, the viscoelastic dampening ability. This may lead to a redistribution of mechanical loads between the intervertebral disc and the facet joints. Moreover the insertion of rotation centers without lateral translations modifies the dynamics of the spine.

Thus, it is desirable to design and manufacture an intervertebral implant that better mimics the physiological motions of the natural spine.

BRIEF SUMMARY OF THE INVENTION

The present invention relates generally to an implant. More specifically, the present invention relates to a flexible connector that may be used as an intervertebral implant for implantation into an intervertebral disc space between adjacent vertebral bodies.

In an embodiment, a flexible connector comprises a first end plate and a second end plate, a strut portion including a first pair of opposing struts connected to the first end plate and a second pair of opposing struts connected to the second end plate, and a beam interposed between the first and second endplate and connected at a first end with the first pair of opposing struts and connected at a second end with the second pair of opposing struts. Each strut of the first pair of opposing struts are preferably connected on opposite ends of an outer surface of the first end plate and each strut of the first pair of opposing struts extends in a substantially perpendicular direction away from an inner surface of the first end plate towards and inner surface of the second endplate.

In a further embodiment in which the flexible connector is used as an implant for insertion into an intervertebral disc space between first and second vertebral bodies, the implant comprises a superior implant end plate having a superior top surface for contacting the first vertebral body, a superior outer surface, and a superior inner surface. The superior implant end plate includes a first superior strut and a second superior strut each connected at a first end to an opposing side of the superior implant end plate near the superior outer surface, and preferably extends away from the superior inner surface in a substantially perpendicular direction. The first and second superior struts each have a curved portion extending inwardly towards one another. A hanging beam may be positioned substantially parallel to the first and second superior struts and may be connected at a first end to each of the curved portions of the first and second superior struts. An inferior implant end plate has an inferior top surface for contacting the second vertebral body, an inferior outer surface, and an inferior inner surface. The inferior implant end plate includes a first inferior strut and a second inferior strut each of which is connected at a first end to an opposing side of the inferior implant end plate near the inferior outer surface, and preferably extending away from the inferior inner surface in a substantially perpendicular direction. The first and second inferior struts each have a curved portion extending inwardly towards one another and connecting with a second end of the hanging beam.

In a preferred embodiment of the implant, the first and second superior struts of the superior implant end plate and the first and second inferior struts of the inferior implant end plate are positioned substantially within a plane of the superior and inferior outer surfaces.

A method for inserting an intervertebral implant into a disc space between a first vertebral body and a second vertebral body with an insertion and guide instrument is also disclosed. In an embodiment of this method, the implant includes a first end plate and a second end plate, a strut portion including a first pair of opposing struts connected to the first end plate and a second pair of opposing struts connected to the second end plate, and a beam interposed between the first and second endplate and connected at a first end with the first pair of opposing struts and connected at a second end with the second pair of opposing struts. The method of inserted such an implant comprises a) coupling the implant to the insertion and guide instrument, b) forming a passageway to the disc space, c) inserting the implant into the disc space through the passageway with the insertion and guide instrument, such that the first end plate contacts the first vertebral body and the second end plate contacts the second vertebral body, and d) closing the passageway.

In one preferred embodiment of such a method, the passageway for inserting the intervertebral implant is via a direct lateral trans-psoas approach and the incision is closed without providing any additional supplemental rigid fixation to secure the implant to the adjacent vertebral bodies.

Additional features and advantages of the present invention are described further below. This summary section is meant merely to illustrate certain features of the embodiments of the inventions, and is not meant to limit the scope of the invention in any way. The failure to disclose a specific feature or embodiment of the invention, or the inclusion of one or more features in this summary section, should not be construed to limit the invention as claimed.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating preferred embodiments of the intervertebral implant and associated method of use of the present invention, drawings of the preferred embodiments are shown. It should be understood, however, that the application is not limited to the precise arrangement, structures, features, embodiments, aspects, and instrumentalities shown, and that the arrangements, structures, features, embodiments, aspects and instrumentalities shown may be used singularly or in combination with other arrangements, structures, features, aspects, embodiments and instrumentalities. In the drawings.

DETAILED DESCRIPTION OF THE INVENTION

Certain terminology is used in the following description for convenience only and is not limiting. The words "right", "left", "lower", "upper", "top", and "bottom" designate directions in the drawings to which reference is made. The words "inwardly" or "distally" and "outwardly" or "proximally" refer to directions toward and away from, respectively, the geometric center of the intervertebral implant, spacer, blade elements and related parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Similar reference numerals will be utilized throughout the application to describe similar or the same components of each of the preferred embodiments of the implant described herein and the descriptions will focus on the specific features of the individual embodiments that distinguish the particular embodiment from the others.

Preferred embodiments of the present application are directed to a flexible intervertebral implant 1, 200, 300, 600 ("1-600"). It should be understood that while the various embodiments of the flexible intervertebral implant 1-600 will be described in connection with spinal surgery, those skilled in the art will appreciate that the flexible intervertebral implant 1-600, as well as the components thereof, may be used for implantation into other parts of the body, including, for example, long bones or bones in the hand, face, feet, extremities or nearly any bone in the human body including the knee, hip, shoulder, finger or other joint replacement or for bone augmentation. By way of further example, the strut or pendulum principle of the present invention may also be applied to any implant or medical device, or parts thereof, to create one or more flexible sections. By way of non-limiting example, the strut or pendulum principle may be applied to bone anchors, plates, rods, intramedullary nails, endoprosthesis stems, etc. For example, referring to FIG. 7, one possible alternative use of the strut or pendulum principle is in a femoral and trochanter nail. Advantages of the flexible element are that stresses on the nail will be better distributed and the nail will therefore be more likely prevented from migration or backing out. This is particularly advantageous when inserted in softer or osteoporotic bone.

The flexible intervertebral implant 1-600 is preferably sized and configured to be implanted between adjacent vertebral bodies V. The implant 1-600 may be sized and configured to replace all or substantially all of an intervertebral disc space D between adjacent vertebral bodies V or only part of the intervertebral disc space D. In addition, the implant 1-600 may be configured to replace an entire vertebral body V and related disc spaces D or multiple disc spaces D in a patient's spine, as would be apparent to one having ordinary skill in the art based upon a review of the present application. The implant 1-600 may be adapted for use in the anterior, antero-lateral, direct lateral, extra-foraminal, transforaminal, and posterior approaches for insertion into the spine.

Referring to FIGS. 1-3 and 6A-6C, the implant 1-600 preferably includes a superior endplate 3, an inferior endplate 5, and one or more struts 10, 20, and one or more hanging beams or pendulum type members 50. As shown, the struts 10, 20 generally extend vertically from (or in a substantially perpendicular direction relative to) one of the superior and inferior endplates 3, 5 and include one or more, and more preferably two or more, horizontal bends or curves 30, 40. The bends 30, 40 provide interconnection between the struts 10 extending from the superior endplate 3, to a first end 52 of the one or more hanging beams 50, and interconnection between the struts 20 extending from the inferior endplate 5 to a second end 54 of the one or more hanging beams 50. As further described below, in connection with FIGS. 4A and 4B, the above-described interconnection between the struts 10 and 20 and the hanging beams 50 allows the superior and inferior endplates 3, 5 to move, compress and/or flex with respect to one another.

Figure 1A:
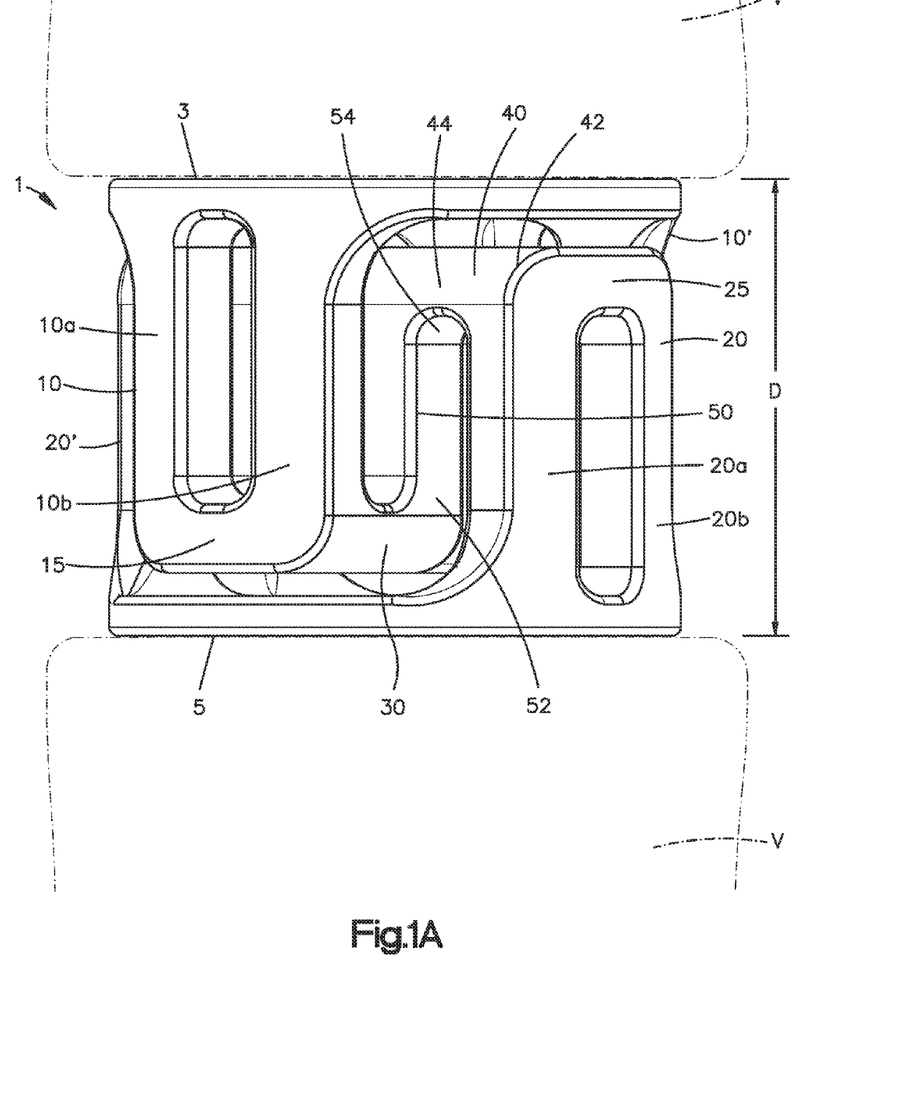
FIGS. 1A-1C illustrate various views of an intervertebral implant according to a first preferred embodiment of the present application.
Figure 1B:
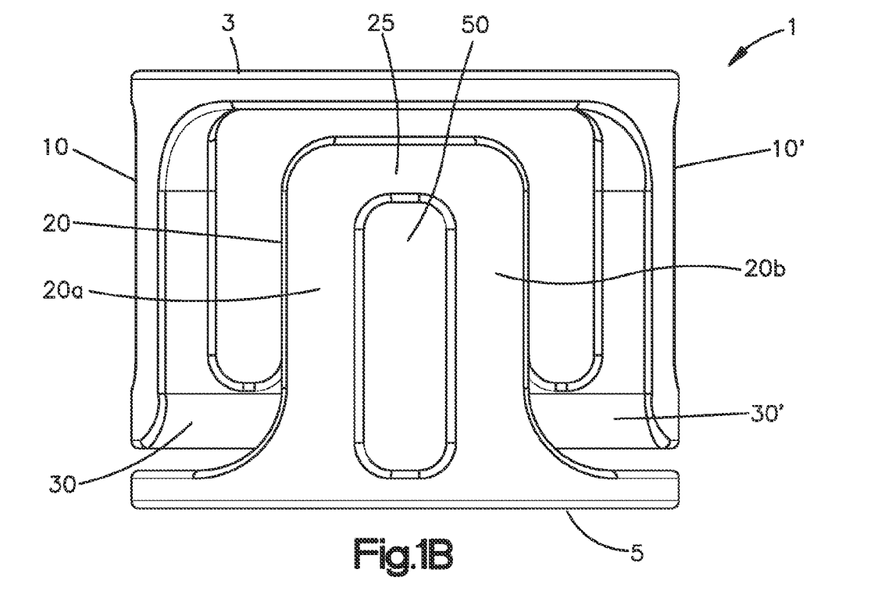
Figure 1C:
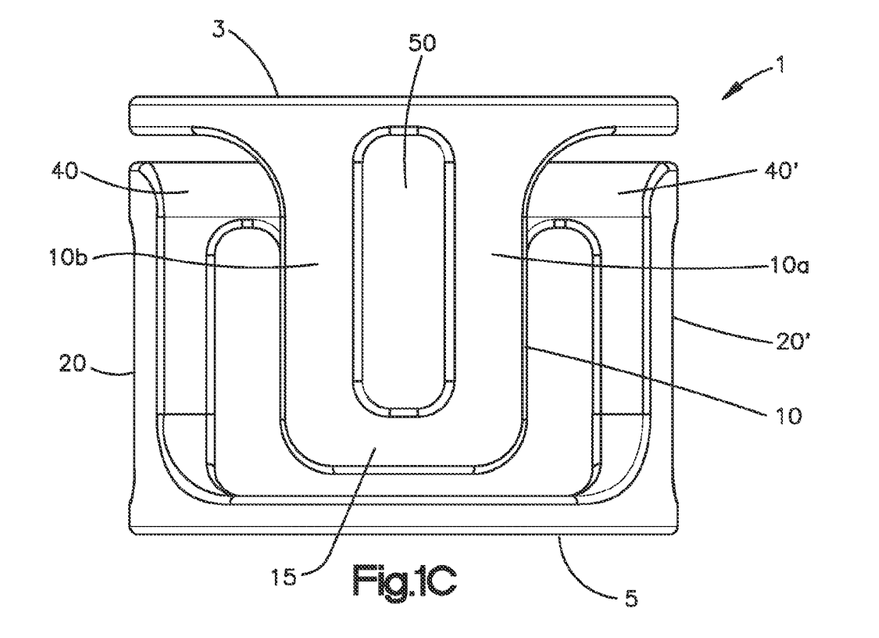

Referring to FIGS. 1A-1C in the first preferred embodiment of the implant 1, each of the superior and inferior endplates 3, 5 include two pair of struts 10, 10' and 20, 20'. Each pair of struts 10, 10' and 20, 20' includes a respective first bend 15, 25 that interconnects a first strut 10a, 20a of a strut pair (e.g., strut 10', 20') with a respective second strut 10b, 20b of the strut pair (e.g., strut 10b, 20b). Thus, with respect to the struts 10, 10' extending from the superior endplate 3, strut 10a is connected to strut 10b by bend 15. In FIG. 1A the second pair of struts 10' is not visible. FIG. 1B shows a side elevation view depicting both strut pairs 10, 10' of the superior endplate 3. Similarly, for the struts 20, 20' extending from the inferior endplate 5, strut 20a is connected to strut 20b by bend 25. FIG. 1C shows a side elevation view depicting both strut pairs 20, 20' of the inferior end plate 5.

Implant 1 further includes second and third bends 30, 40, which connect each pair of struts 10, 10' to the hanging beam 50. More specifically, bend 30, which is connected at one end to the struts 10, 10' of the superior endplate 3, extends horizontally towards an interior of the implant 1 and is connected at an opposite end to a first end 52 of at least one of the hanging beams 50. Bend 40, which is connected at one end 42 to the struts 20, 20' of the inferior endplate 5, extends horizontally towards an interior of implant 1 and is connected at an opposite end 44 to a second end 54 of the hanging beam 50.

Thus, a strut 10 may extend away from the superior endplate 3 in a substantially perpendicular direction relative to the superior end plate 3 towards the inferior endplate 5 and, before contacting the inferior endplate 5, bend in a horizontal direction, either laterally, anterior-posterior, both, or some combination of both, until it contacts a hanging beam 50. The hanging beam 50 extends in a substantially perpendicular direction relative to the superior end plate 3 back towards the superior endplate 3. Next, at an opposite end of the hanging beam 50, another bend in a horizontal direction either laterally, anterior-posterior, both, or some combination of both, extends towards an exterior of the implant 1, until it contacts one of the struts 20, 20' of the inferior endplate 5.

Figure 2:
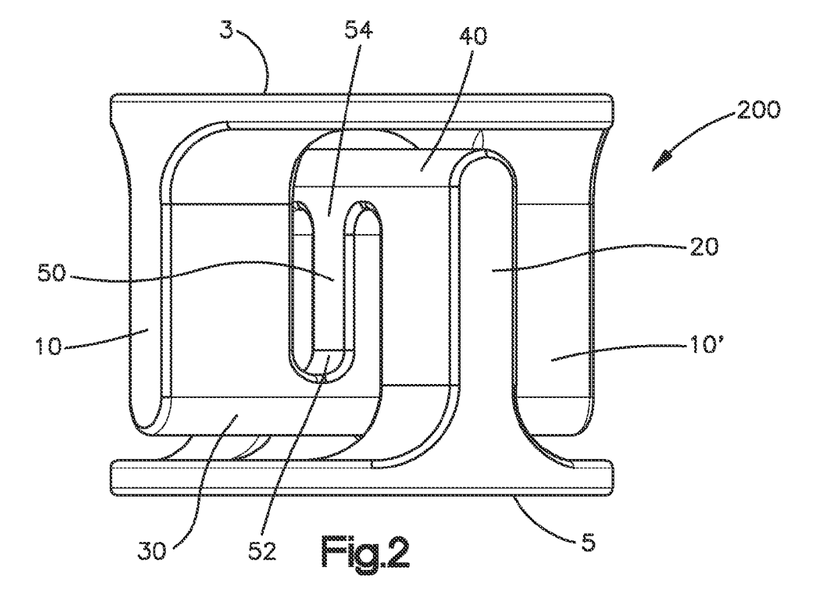
FIG. 2 illustrates a side elevational view of an intervertebral implant according to a second preferred embodiment of the present application.

Referring to FIG. 2 in a second preferred embodiment of the implant 200, each of the superior and inferior endplates 3, 5 includes a single strut 10 and 20. Each strut 10 and 20 includes a bend 30, 40 that interconnects each strut to a single hanging beam 50. More specifically, each of the bend 30, 40, which are connected at one end to the respective struts 10, 20 of the superior and inferior endplates 3, 5, extend horizontally towards an interior of the implant 200 and are connected at an opposite end (52 or 54) of the hanging beam 50.

Thus, a strut 10, 10' may extend away from the superior endplate 3 in a direction substantially perpendicular relative to the superior end plate 3 towards the inferior endplate 5 and, before contacting the inferior endplate 5, bending in a horizontal direction, either laterally, anterior-posterior, both, or some combination of both, until it contacts the hanging beam 50 at an end 52. The hanging beam 50 extends in a direction substantially perpendicular relative to the superior end plate 3 back towards the superior endplate 3. Next, at an opposite end 54 of the hanging beam 50, another bend in a horizontal direction either laterally, anterior-posterior, both, or some combination of both, extends towards an exterior of the implant 200, until it contacts the strut 20, 20' of the inferior endplate 5.

Figure 3:
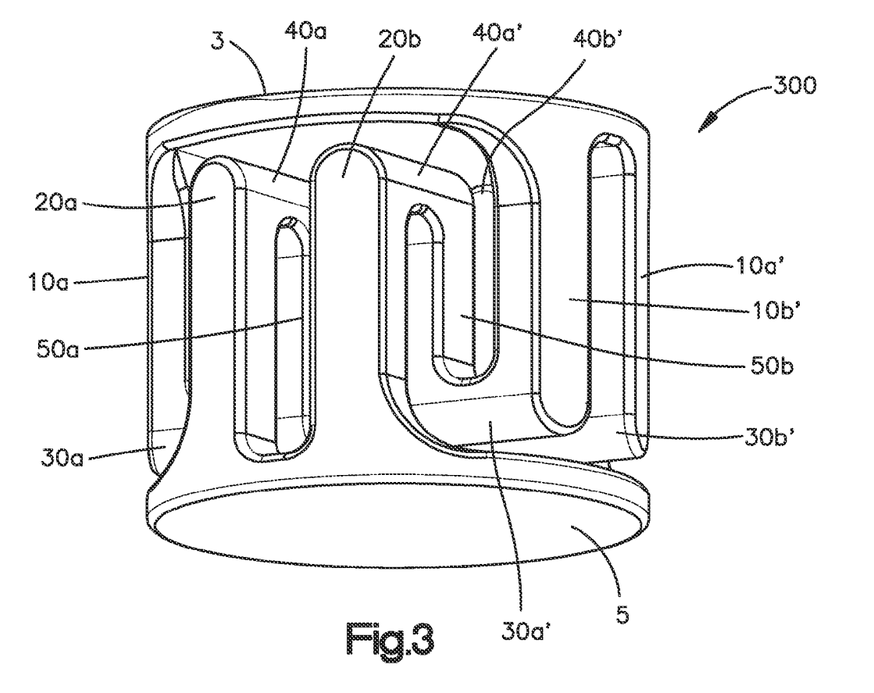
FIG. 3 illustrates a side elevational view of an intervertebral implant according to a third preferred embodiment of the present application.

Referring to FIG. 3 in a third preferred embodiment of the implant 300, each of the superior and inferior endplates 3, 5 includes two pair of struts 10, 10' and 20, 20'. Unlike the first preferred embodiment of the implant 1 shown in FIGS. 1A-1C, each pair of struts 10, 10' and 20, 20' is not interconnected. Instead, each of strut 10a and 10b (and respective struts 10a' and 10b') of strut pairs 10, 10' of the superior endplate 3 includes a respective bend 30a, 30b, 30a', 30b' that connects that strut to a respective hanging beam 50a, 50b, 50a', 50b'. Because each strut (four in total in this embodiment for each of the superior and inferior endplates) includes a bend that connects it to a separate hanging beam, the third preferred embodiment of implant 300 includes four hanging beams. More specifically, for example, bend 30a, which is connected at one end to one of the struts 10a of the superior endplate 3, extends horizontally towards an interior of implant 300 and is connected at an opposite end to a first end of one of the hanging beams 50a. Similarly, for example, bend 40a, which is connected at one end to one of the struts 20a of the inferior endplate 5, extends horizontally towards an interior of implant 300 and is connected at an opposite end to a second end of hanging beam 50a.

It is envisioned that the flexible intervertebral implant 1-600 may include any number of struts 10, 20, bends 30, 40, and hanging beams 50, as may be deemed necessary to achieve a particular design criteria. As will be generally appreciated by one of ordinary skill in the art, the number of struts 10, 20, the number of bends 30, 40, the number of hanging beams 50, the cross-sectional shape of the struts 10, 20, bends 30, 40, and beams 50, the selected material for the flexible intervertebral implant, the exterior and/or interior surface characteristics, etc., can be varied to tailor the stiffness and position holding characteristics for the flexible element/implant.

The top surface of the superior endplates 3 and the bottom surface of the inferior endplate 5, may include a series of teeth, ridges, spikes or other similar projections (see projections 613 in FIGS. 6A-6C) to aid in securing the flexible intervertebral implant 1-600 to the end plates of the adjacent vertebral bodies V. Alternatively, and/or in addition, the flexible intervertebral implant 1-600 may include one or more bone fixation elements 650, 652, 654, 656, such as bone screws (referring to again to FIGS. 6A-6C), and/or the top and bottom surfaces of the superior and inferior endplates, respectively, may include one or more keels (not shown) for securing the intervertebral flexible intervertebral implant 1-600 to the adjacent vertebral bodies V.

The top and bottom surfaces of the superior and inferior endplates 3, 5 respectively, may also include a curved or a tapered surface to help provide an anatomical shape for mating with the patient's spine, to mate with a surface of one of the fractured bone portions or to orient the endplates of the adjacent vertebral bodies V in a desired manner. The particular surface shape and curvature, taper or alternate surface feature in the anterior-posterior direction, as well as the particular surface shape and curvature, taper or alternate surface feature in the medial-lateral direction will depend upon the location where the intervertebral implant 1-600 is intended to be implanted and/or surgeon preferences or whether the implant 1-600 is utilized in a long bone or other area in the body.

As will be appreciated by one of ordinary skill in the art, the flexible intervertebral implant 1-600 may also be coated with various compounds to increase bony on-growth or in-growth, promote healing, or allow for revision of the implant, including hydroxyapatite, titanium-nickel, vapor plasma spray deposition of titanium, or plasma treatment to make the surface hydrophilic.

Figure 4:
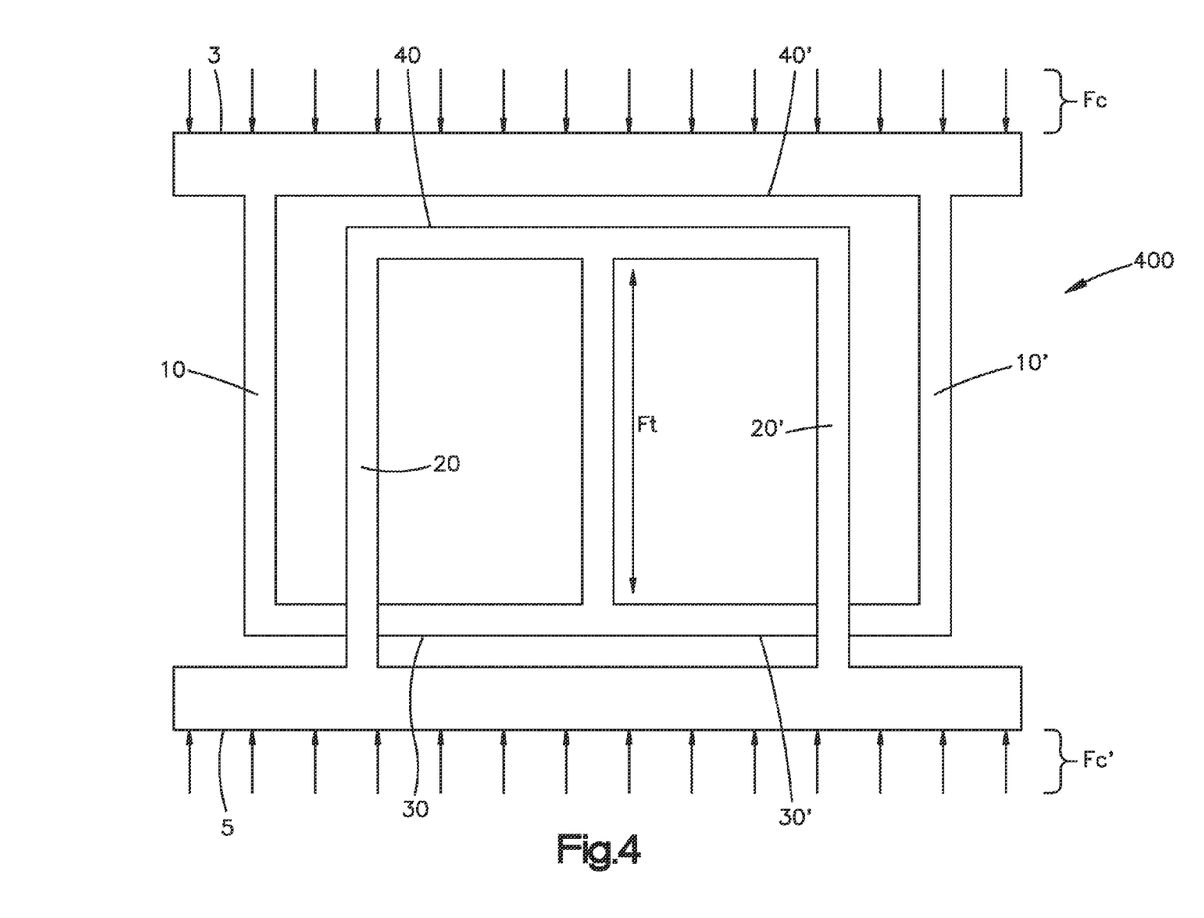
FIG. 4 illustrates a side view of the representative forces acting on the intervertebral implant of FIG. 1 when inserted into an intervertebral disc space between adjacent vertebral bodies.

With reference now to FIG. 4, there is shown an illustration of how the hanging beam configuration of the embodiments of the present invention operate. As shown in FIG. 4, when the implant representation 400 is positioned between vertebrae V, as shown in FIG. 1, forces $F_c$ and $F_c'$ act on the superior and inferior endplates 3 and 5. More specifically, forces $F_c$ and $F_c'$ generally produce a compression force that pushes endplates 3, 5 in a direction substantially inward towards one another. It will be understood, by persons of ordinary skill in the art that such forces $F_c$ and $F_c'$ can vary in their respective angular direction. In other words, it should be understood and a bending force that, for example, causes an edge of one of the endplates 3, 5 to be forced inward such that said endplate 3 or 5, as applicable, is now at an angle relative to the other endplate 3 or 5. Such a bending force $F_c$ or $F_c'$ transmitted through the struts 10 or 20 of the endplate 3 or 5 being forced inward and ultimately to the hanging beam 50. Whether the forces $F_c$ and $F_c'$ are substantially normal to the endplates 3, 5, or are at some angle, the forces are transmitted through the respective struts 10, 10' of the superior endplate 3 and struts 20, 20' of the inferior endplate 5 to the horizontal bends 30, 30' of the superior endplate 3 and horizontal bends 40, 40' of the inferior endplate 5. Due to the compression forces $F_c$ and $F_c'$, the respective horizontal bends 30, 30' of the superior endplate 3 and horizontal bends 40, 40' of the inferior endplate 5 are forced away from one another thereby causing a tension force $F_t$ to be realized by the hanging beam 50. Again, depending on whether the forces $F_c$ and $F_c'$ are normal or at some angle will have an impact on the angular nature of the tension force $F_t$ realized by the hanging beam 50.

One advantage of the configurations of the various embodiments of the implant 1-600 of the present invention is that the incorporation of one or more struts 10, 20 enables dampening and/or compression of the implant 1-600 and specifically of the superior and inferior endplates 3, 5 with respect to one another. In addition, incorporation of one or more struts 10, 20 enables at least six (6) degrees of freedom while motion and rotation of the implant 1-600 is limited thanks to the intrinsic structure of the metal struts. The implant 1-600 may include one or more mechanical stops (not shown) to prevent the implant 1-600 from over extension.

Figure 5A:
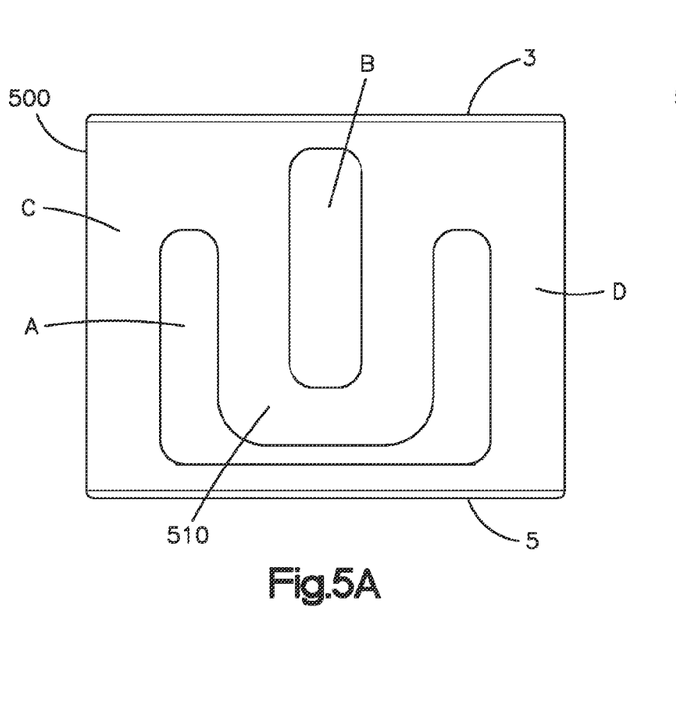
FIGS. 5A and 5B are side elevational views of various milling stages of the intervertebral implant of FIG. 1.
Figure 5B:
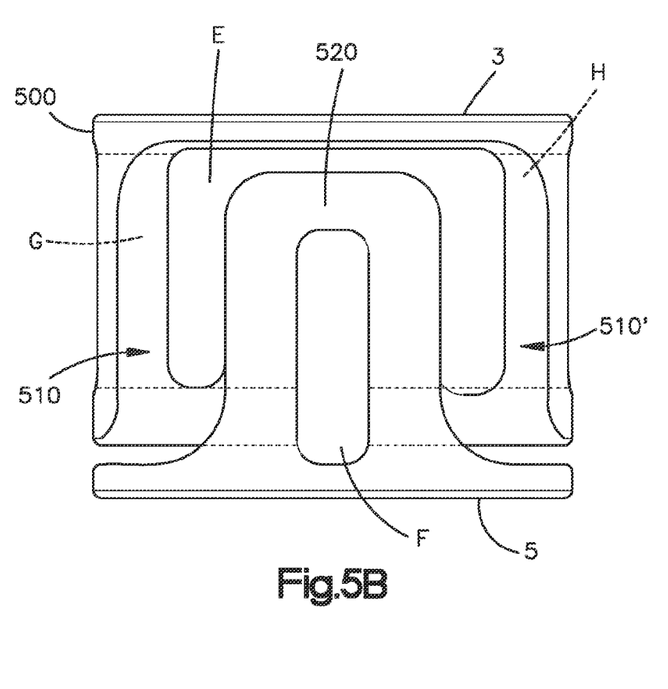

As shown in the embodiments previously described, the one or more struts 10, 20, and hanging beam 50, are operatively coupled to the superior and inferior endplates 3, 5. The struts 10, 20 can be coupled to the endplates 3, 5 by any mechanism known in the art including but not limited to via welding, tacking, adhesive, hinges, a fixation device (e.g., screws or rivets), or any other means of fixation now known or hereafter developed. Alternatively, the implant 1-600 can be manufactured as a single, integral piece, as shown in FIGS. 5A and 5B, discussed below, which illustrates some exemplary manufacturing principles for manufacturing the implant 1-600 as a single, integral piece.

In use, the superior and inferior bone contacting endplates 3,5 may be initially inserted into the disc space between vertebral bodies V prior to inserting the one or more struts 10, 20 and hanging beams 50, which may thereafter be inserted between the endplates 3, 5. Alternatively, the implant 1-600 may be initially assembly and then inserted as a unit. Other variants would be forming the implant 1-600 as a single, integral unit.

In contrast with current implant design, incorporating one or more struts 10, 20, and hanging beams 50, enables the implant 1-600 to withstand high axial forces while still allowing sufficient flexibility for bending. In addition, because the implant 1-600 does not contain any articulating surfaces, no abrasion particles will be created during normal use of the implant 1-600. That is, in current metal implants, the mobility of the implant 1-600 may be provided via articulating members. Due to the dynamic behavior under loading material debris often is an inevitable side effect. In contrast, the present implant 1-600 does not generate material debris because the components do not touch each other.

The superior and inferior endplates 3,5 can be manufactured from any biocompatible material including but not limited to nitinol or other memory metals, high flexible metals, plastics, reinforced plastics and combinations thereof. For example, depending on the required flexibility and endurance requirements, the implant 1-600 can be manufactured from stainless steel, cobalt chromium, nitinol or plastics. The implant 1-600 can also be manufactured via conventional techniques. Alternatively, the implant 1-600 can be manufactured via injection molding. Preferably, the superior and inferior endplates 3, 5 are manufactured from titanium or a titanium alloy for it's osseo-conductive characteristics. The one or more struts 10,20 are preferably manufactured from CoCr or other elastic or super elastic metal for it's relevant material/fatigue properties and biocompatible character. Other material combinations are also possible.

Referring now to FIGS. 5A and 5B, there is shown a preferred method of milling an embodiment of the flexible element/implant 1-600. The starting point is preferably a body 500 sized and shaped roughly to the outer dimensions of the desired final flexible implant 1-600. Body 500 may be substantially cylindrical in shape, or shaped to have a square, rectangle, kidney, or other cross-sectional shape as a matter of design choice. It will be understood that, although the figures show only one side of body 500 in a two-dimensional illustration, the milling steps described below are generally performed as pairs, such that both sides of the body 500 are milled as mirror images. In a first milling step, areas A and B, as shown in FIG. 5A, are milled away to produce a first strut pair 510, which for example correspond to strut pairs 10 and 10' of FIGS. 1A and 1B. To complete the milling of the first strut pair 510, and to begin milling of a second strut pair 520, sections C and D may then milled. As shown, in FIG. 5B, body 500 may then be rotated 90-degrees about an axis parallel to the side surface of body 500. In a second milling step, areas E and F, as shown in FIG. 5B, are milled away to produce a second strut pair 520, which for example correspond to strut pairs 20 and 20' of FIGS. 1A and 1C. To complete the milling of the second strut pair 520, sections G and H may then milled.

It is envisioned that the flexible implant 1-600 may be used as a main or supporting construct. If used as a supporting construct, the flexible implant 1-600 may be used in combination with, for example, a thermoplastic visco-elastic dampening feature (not shown). This would result in load-sharing between the implant 1-600 and the thermoplastic visco-elastic damper. Furthermore, in this co-sharing concept, the central part can be completely molded-in and filled up, as well as just surrounded by a separate visco-elastic ring. The principle can be applied to create a strain-regulating cage for insertion between two adjacent, opposing vertebral bodies V. The cage allows limited motion, which stimulates bone growth with the natural bone. Over the design parameters, the stiffness can be managed to mimic the stiffness of the natural bone. Due to the high-load carrying characteristic of the strut construction, large recesses can be created for bone graft placement. That is, the cage can be constructed in a way that stress absorbed by the cage is transferred to the graft material inserted into a hollow inner cavity formed in the cage, thus allowing ideal strain levels to be attained in the graft material under minimal loads, while also offering a level of protection to the graft material preventing mechanical failure of the graft material due to high strains.

Figure 6A:
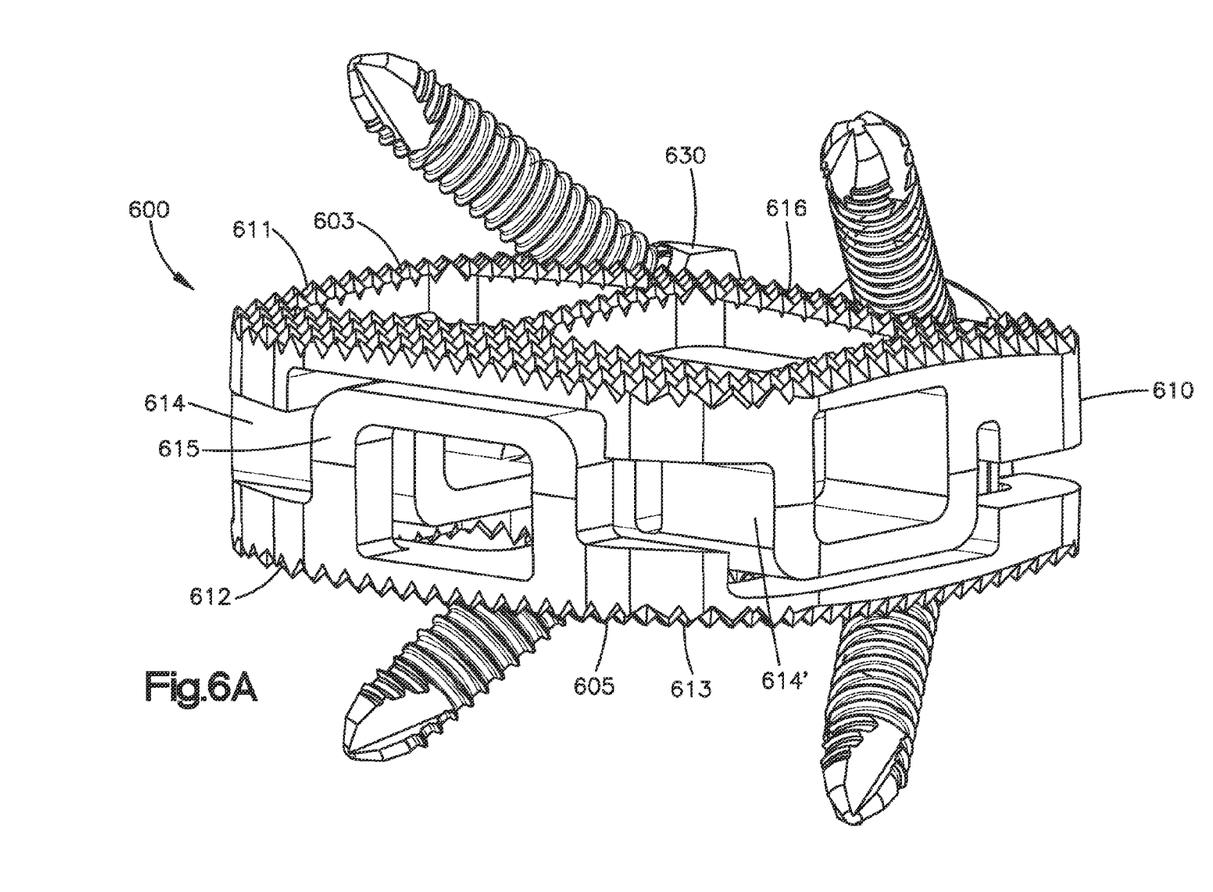
FIGS. 6A-6D illustrate various views of an intervertebral implant according to a fourth preferred embodiment.
Figure 6B:
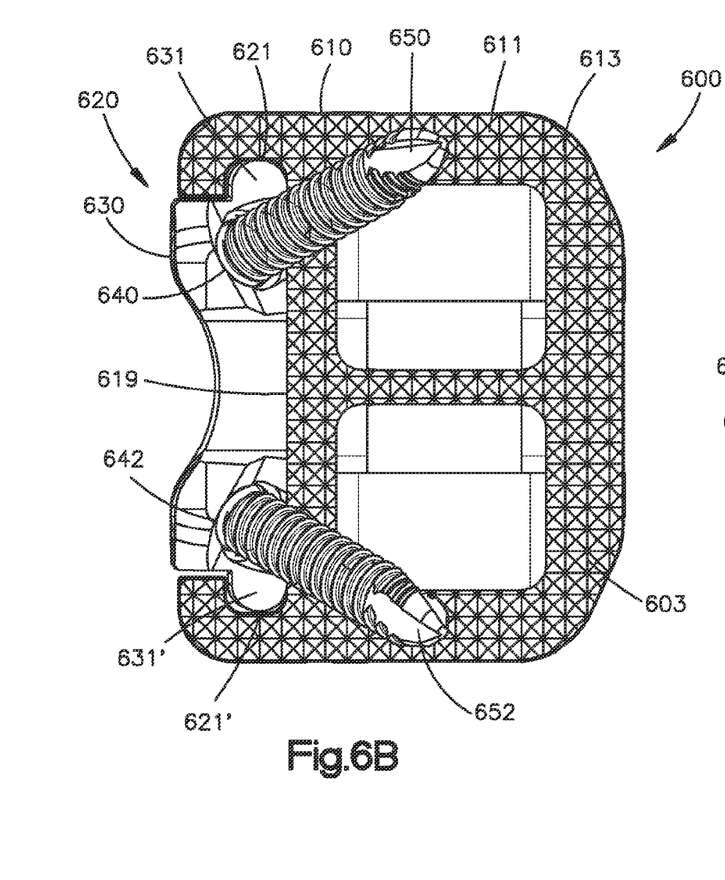
Figure 6C:
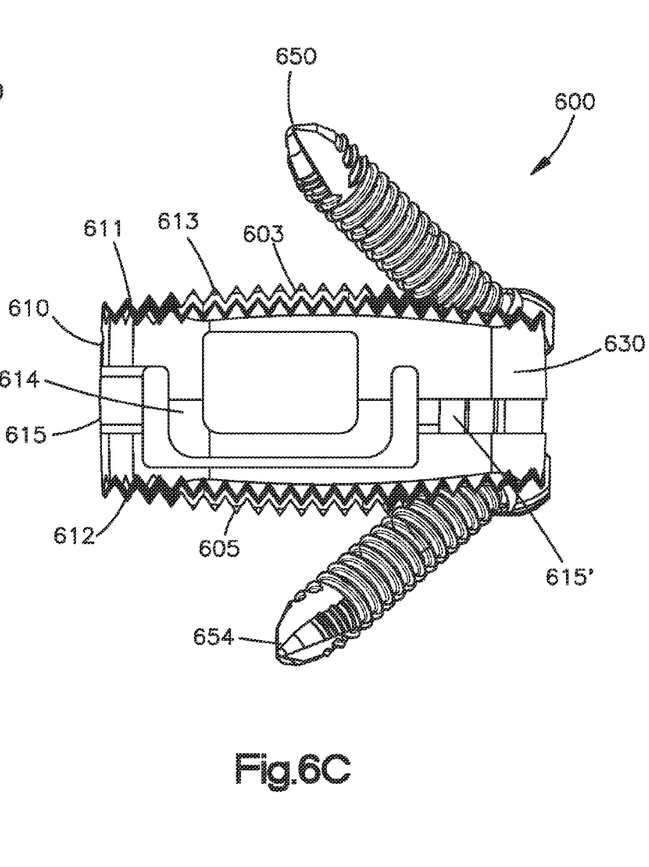

Referring to FIGS. 6A-6D, a fourth preferred embodiment of the implant 600 includes a spacer portion 610, a plate portion 630, and may also include any number of supporting elements, such as one or more blade elements (not shown). The spacer portion 610 is preferably configured similar to one of the first through third preferred embodiments of the flexible implant 1-600 described above. However, the spacer portion 610 may be shaped to be generally rectangular in cross-section with a relatively stout profile, such that its height is substantially smaller than its length and width, as best shown in FIGS. 6A and 6B.

The spacer portion 610 generally includes a superior surface 611 and an inferior surface 612. Each of the superior surface 611 and the inferior surface 612 preferably includes a plurality of teeth, ridges, spikes or other similar projections to aid in securing the implant 600 to the endplates of the adjacent vertebral bodies V. As shown in FIGS. 6A-6D, projections 613 are formed as a series of pyramidal spikes. The spacer portion 610 also generally includes two struts pairs 614, 614' and 615, 615' (see FIG. 6C) for each of the superior and inferior surfaces 611, 612. The configuration shown in FIGS. 6A-6D is generally consistent with the first embodiment shown in FIGS. 1A-1C, but may incorporate any of the first through third embodiments shown in FIGS. 1-3.

The plate portion 630 is preferably mounted to the trailing surface 616 of the spacer portion 610 and preferably does not greatly increase the vertical or lateral perimeter of the interbody spacer portion 610. That is, the height of the plate portion 630 is preferably no more than the height of the interbody spacer portion 610 so that the plate portion 630 does not substantially increase the height profile of the interbody spacer portion 610 and the width of the plate portion 630 does not substantially extend beyond a width of the spacer portion 610. In this manner, the intervertebral implant 600 has a relatively low profile. Additionally, in this manner, the plate portion 630 may be entirely implanted into the intervertebral disc space D between the adjacent vertebral bodies V such that the plate portion 630 does not extend beyond an edge of the disc space D.

In use, the plate portion 630 may be sized and configured so that the top and bottom surfaces of the plate portion 630 contact the endplates of the adjacent vertebral bodies V. Alternatively, the plate portion 630 may be sized and configured so that only the spacer 610 contacts the adjacent vertebral bodies V. For example, the height of the plate portion 630 may be small enough so that it does not contact the vertebral bodies V when connected to the spacer portion 610 in an implanted position.

The plate portion 630 may be coupled to the interbody spacer portion 610 by any coupling mechanism now or hereafter known. For example, the spacer portion 610 may include one or more recesses 619 (shown in FIG. 6B) formed in the side or trailing surfaces for engaging one or more projections 631, 631' (shown again in FIGS. 6A and 6C) extending from the plate portion 630.

More specifically, as shown in FIG. 6B, the spacer portion 610 includes a recess 619 formed in the side or trailing surfaces for engaging a pair of opposed projections 631, 631' extending from the plate portion 630. Recess 619 comprises a space 620 formed with a pair of opposing detents 621 and 621' preferably formed at an inside of the space 620 furthest from the outer edge of the spacer portion 610. In the preferred embodiment shown in FIG. 6C, the size and shape of the plate portion 630, including the pair of opposed projections 631, 631', is configured to fit within space 620 with tolerances tight enough to cause plate portion 630 to be fixed to spacer portion 610.

Alternatively, plate portion 630 may be formed integrally with spacer portion 610. Other coupling mechanisms for coupling the plate portion 630 to the spacer portion 610 are disclosed in International Application No. PCT/US2008/082473 filed on Nov. 5, 2008 and entitled, "Low Profile Intervertebral Implant," the contents of which are hereby incorporated by reference in their entirety.

Figure 6D:
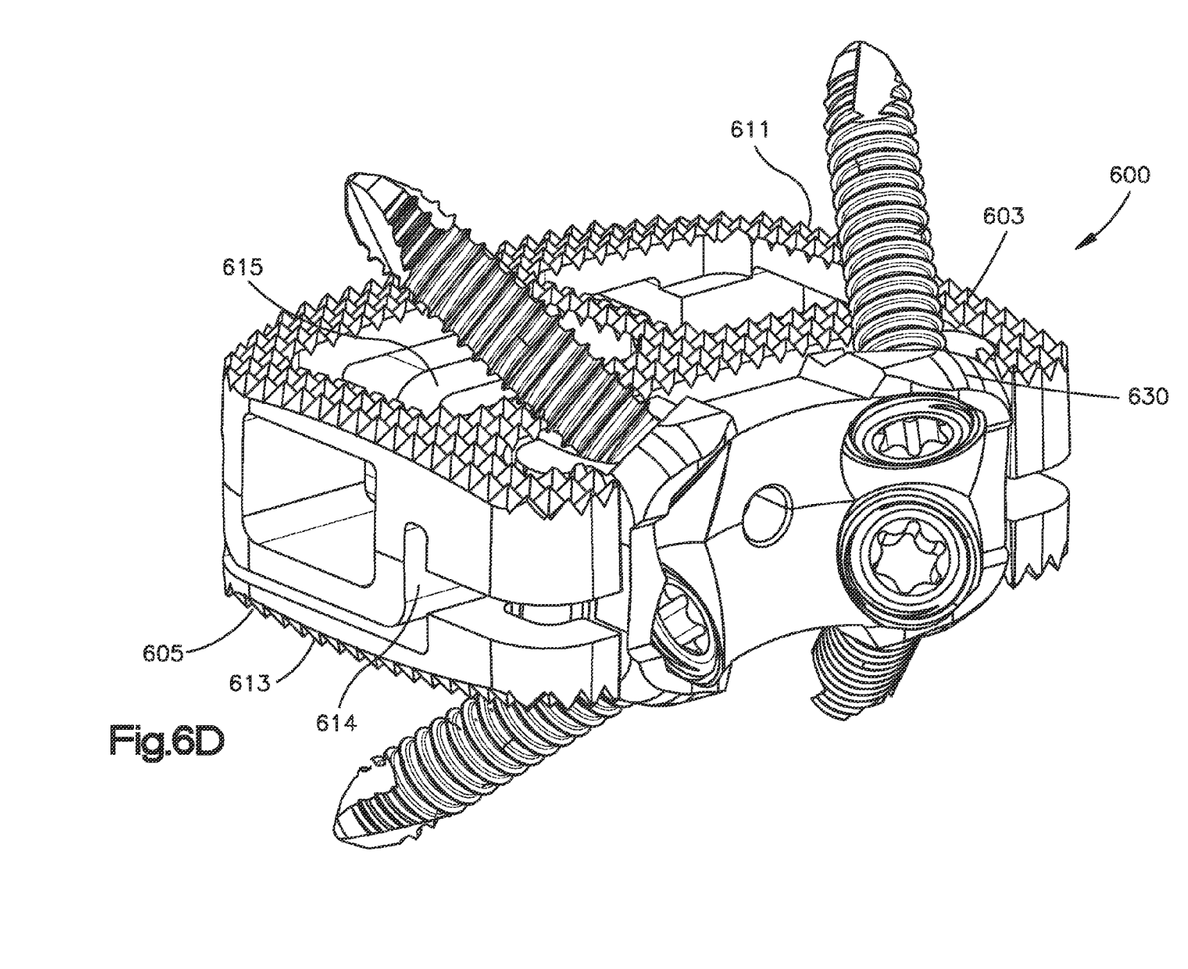

With reference to FIG. 6D, the plate portion 630 also preferably includes a plurality of bone screw receiving holes 640, 642, 644, and 646. The holes may be threaded to receive the bone screws 650, 652, 654, and 656, or may include any other bone screw receiving mechanism as is known in the art. It is preferred that the holes 640, 642, 644, and 646 are formed at an incline relative to the upper and lower surfaces 611, 613 of the spacer portion 610, such that the bone screws 650, 652, 654, and 656 extend at an angle through the plate portion 630 and over the upper and lower surfaces 611, 613. The bone screws 650, 652, 654, and 656 can, therefore, extend into the respective vertebral bodies into which the fusion cage 600 will be placed.

The spacer portion 610 may be constructed of any biocompatible material or combination of materials as previously described. The plate portion 630 may be formed of a different material than the spacer 610. For example, the plate portion 630 may be formed of a metallic material such as, a titanium or a titanium alloy, or a polymer such as, PEEK. The plate portion 630 and the spacer 610 may be formed from the same material. For example, the plate portion 630 and the spacer 610 may both be constructed of tantalum nitride (TaN).

In use, the spacer portion 610 and the plate portion 630 may be inserted into the desired intervertebral disc space D or void created by the removal of at least a portion of an intervertebral disc.

The strut or pendulum principle may also be applied to any implant or medical device, or parts thereof, to create one or more flexible sections. By way of non-limiting example, the strut or pendulum principle may be applied to bone anchors, plates, rods, intramedullary nails, endoprosthesis stems, etc. For example, referring to FIG. 7, one possible alternative use of the strut or pendulum principle is in a femoral and trochanter nail. Advantages of the flexible element are that stresses on the nail will be better distributed and the nail will therefore be more likely prevented from migration or backing out. This is particularly advantageous when such a nail is inserted in softer or osteoporotic bone.

Figure 7:
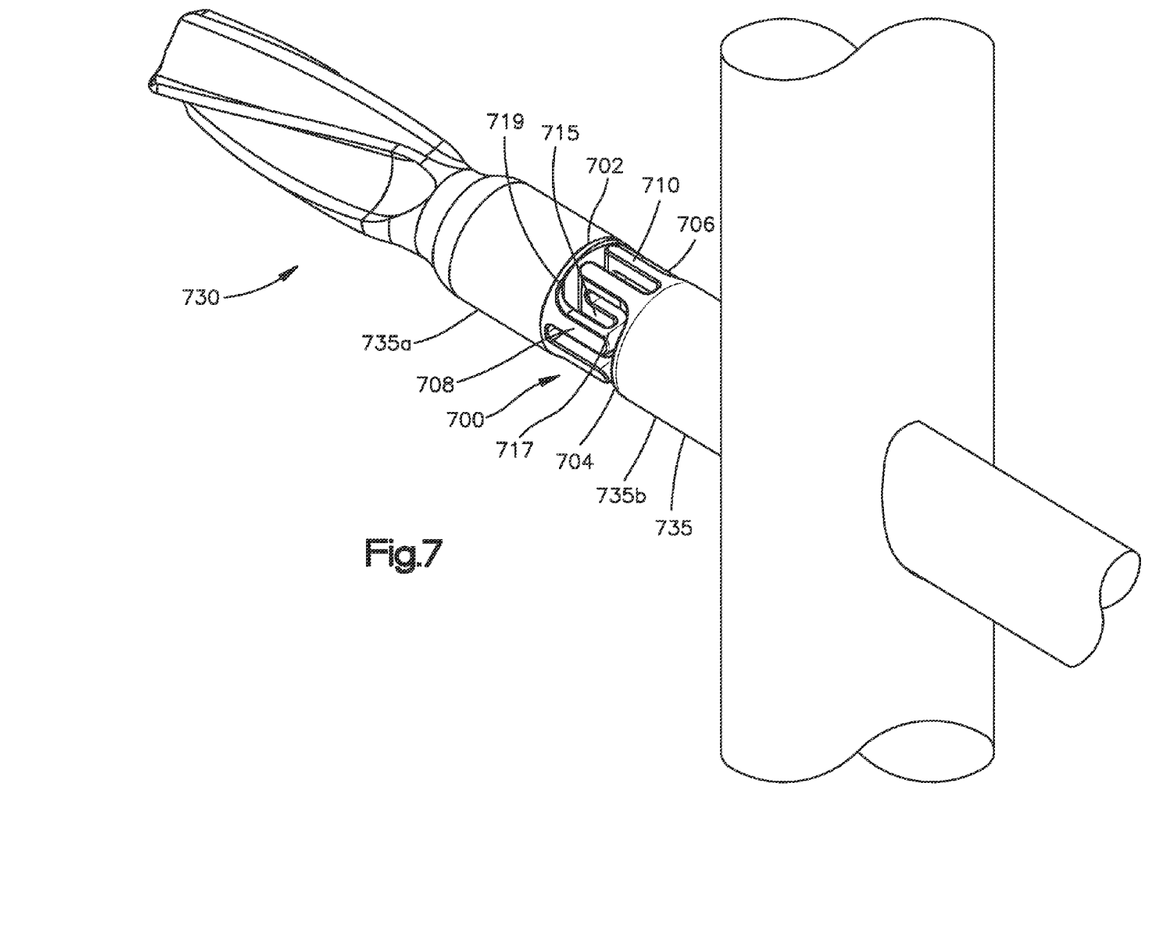
FIG. 7 illustrates an exemplary use of a flexible element according to an embodiment of the present application in conjunction with a femoral and trochanter nail.

Referring now to FIG. 7, there is shown a flexible connector 700, which includes a first endplate 702 and a second endplate 704, and a strut portion 706 including a first pair of opposing struts 708 connected to the first endplate 702 and a second pair of opposing struts 710 connected to the second endplate 704. The strut portion 706 further includes at least one beam 715 interposed between the first and second endplates 702, 704 and connected at a first end 717 with the first pair of opposing struts 708 and connected at a second end 719 with the second pair of opposing struts 710. It will be understood that the flexible connector 700 may be configured according to any of the embodiments disclosed herein, including without limitation those shown in FIGS. 1A-1C and 2-3.

As further shown in FIG. 7, the flexible connector forms part of a femoral or trochanter nail 730. The nail 730 includes a shaft 735 in which the flexible connector 700 is interposed as part of the shaft between shaft parts 735a and 735b. The first and second endplates 702, 704 may be fixed (or selectively removable) from the shaft parts 735a, 735b in any manner known in the art. The flexible connector 700 may also form part of a shaft of a medical device.

Alternatively, the implant 1-600 or the flexible connector 700 may be inserted between a vertebral body and a modular endplate, or between two modular endplates. The modular endplates may be shaped on one side, for example, to contour to the surfaces of vertebral bodies, and shaped to mate with the endplates of the implant 1-600 or the flexible connector 700. Such an arrangement would permit standardized implants 1-600 or the flexible connectors 700 to be used with modular endplates customized for a particular purpose, including without limitation for insertion between two vertebral bodies. The implant 1-600 or the flexible connector 700 may be connected to such modular implants using a friction fit, through bonding or welding as may be necessary to suit the needs of a particular application.

As will be appreciated by those skilled in the art, any or all of the components described herein may be provided in sets or kits so that the surgeon may select various combinations of components to form an implant and create a disc replacement system which is configured specifically for the particular needs/anatomy of a patient. It should be noted that one or more of each component may be provided in a kit or set, including the instruments and tools. In some kits or sets, the same component or part may be provided in different shapes and/or sizes. The surgeon or staff may mix and match the first and second parts to create the implant before or during the procedure.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

We claim:

1. An intervertebral implant for insertion into an intervertebral disc space between first and second vertebral bodies, the implant comprising:
    a superior implant portion having a superior top surface for contacting the first vertebral body, a superior outer surface, and a superior inner surface, the superior implant portion including a first superior strut and a second superior strut each connected at a first end to an opposing side of the superior implant portion near the superior outer surface, and extending away superior inner surface in a substantially perpendicular direction, the first and second superior struts each having a curved portion extending inwardly towards one another;
    a hanging beam positioned substantially parallel to the first and second superior struts and connected at a first end to each of the curved portions of the first and second superior struts; and
    an inferior implant portion having an inferior top surface for contacting the second vertebral body, an inferior outer surface, and an inferior inner surface, the inferior implant portion including a first inferior strut and a second inferior strut each connected at a first end to an opposing side of the inferior implant portion near the inferior outer surface, and extending away from the inferior inner surface in a substantially perpendicular direction, the first and second inferior struts each having a curved portion extending inwardly towards one another and connecting with a second end of the hanging beam;
    wherein the superior inner surface and the inferior inner surface are in an opposing relationship, and the first and second superior struts of the superior implant portion and the first and second inferior struts of the inferior implant portion are positioned substantially within a plane of the superior and inferior outer surfaces.

2. The intervertebral implant of claim 1, wherein the first and second superior struts of the superior implant portion and the first and second inferior struts of the inferior implant portion are each configured as a strut pair.

3. The intervertebral implant of claim 2, wherein each strut pair of the first and second superior struts of the superior implant portion and the first and second inferior struts of the inferior implant portion are adjoined at the end having the curved portion.

4. The intervertebral implant of claim 3, wherein the superior implant portion includes two strut pairs, and the inferior implant portion includes two strut pairs.

5. The intervertebral implant of claim 2, wherein each strut of the strut pairs of the first and second superior struts of the superior implant portion and the first and second inferior struts of the inferior implant portion include a separate curved portion.

6. The intervertebral implant of claim 5, further comprising at least four hanging beams, wherein each curved portion of each strut of the strut pairs of the superior implant portion and the inferior implant portion are connected to a separate end of one of the four hanging beams.

7. The intervertebral implant of claim 1, wherein the superior implant portion, the inferior portion, the first and second superior struts of the superior implant portion and the first and second inferior struts of the inferior implant portion, and the hanging beam are integrally formed.

8. The intervertebral implant of claim 1, wherein the superior top surface, superior outer surface, inferior top surface, and inferior outer surface define a substantially cylindrical shape.

9. The intervertebral implant of claim 1, wherein the superior top surface, superior outer surface, inferior top surface, and inferior outer surface define a substantially cuboid shape.

10. The intervertebral implant of claim 1, wherein the superior top surface, superior outer surface, inferior top surface, and inferior outer surface define a substantially rectangular cuboid shape.

11. The intervertebral implant of claim 1, wherein the superior top surface, superior outer surface, inferior top surface, and inferior outer surface define a substantially kidney shape.

12. The intervertebral implant of claim 1, wherein the superior top surface and the inferior top surface further comprise a plurality of projections.

13. The intervertebral implant of claim 1, wherein the plurality of projections are pyramidal in shape.

14. The intervertebral implant of claim 1, further comprising:
    a recess formed in the superior and inferior end plates;
    plate portion substantially sized and shaped to be mounted to the recess of the superior and inferior end plates, the plate portion including a plurality of fastener receiving holes; and
    a plurality of fasteners, each of the plurality of fasteners mounted within one of the plurality of fastener receiving holes of the plate portion, wherein the fasteners are configured to extend into and fasten to one of the vertebral bodies.

15. The intervertebral implant of claim 14, a first fastener receiving hole of the plurality of fastener receiving holes is formed at an incline relative to the superior end plate such that one of the fasteners mounted in the first fastener receiving hole will extend at an angle away from the superior top surface, and a second fastener receiving hole of the plurality of fastener receiving holes is formed at an incline relative to the inferior end plate such that one of the fasteners mounted in the second fastener receiving hole will extend at an angle away from the inferior top surface.

* * * * *